(12) United States Patent
Ladtkow et al.

(10) Patent No.: US 8,057,376 B2
(45) Date of Patent: Nov. 15, 2011

(54) BLOOD PROCESSING APPARATUS WITH SEALED DIFFUSER IN OPTICAL CONTROL APPARATUS

(75) Inventors: James R. Ladtkow, Broomfield, CO (US); Joseph A. Scibona, Littleton, CO (US); Jeremy Kolenbrander, Brighton, CO (US)

(73) Assignee: CaridianBCT, Inc., Lakewood, CO (US)

( * ) Notice: Subject to any disclaimer, the term of this patent is extended or adjusted under 35 U.S.C. 154(b) by 515 days.

(21) Appl. No.: 12/241,441

(22) Filed: Sep. 30, 2008

(65) Prior Publication Data

US 2009/0156383 A1    Jun. 18, 2009

Related U.S. Application Data

(60) Provisional application No. 61/014,554, filed on Dec. 18, 2007.

(51) Int. Cl.
*B04B 15/00*    (2006.01)
*G02B 5/02*    (2006.01)
(52) U.S. Cl. .................. 494/10; 359/599; 359/613
(58) Field of Classification Search .......... 494/10, 494/84; 359/599, 613
See application file for complete search history.

(56) References Cited

U.S. PATENT DOCUMENTS

| | | | |
|---|---|---|---|
| 3,391,597 A | 7/1968 | Gropper | |
| 4,151,844 A | 5/1979 | Cullis et al. | |
| 4,493,691 A | 1/1985 | Calari | |
| 4,557,719 A | 12/1985 | Neumann et al. | |
| 4,670,002 A | 6/1987 | Koreeda et al. | |
| 4,724,317 A | 2/1988 | Brown et al. | |
| 4,834,890 A | 5/1989 | Brown et al. | |
| 5,076,911 A | 12/1991 | Brown et al. | |
| 5,104,526 A | 4/1992 | Brown et al. | |
| 5,260,598 A | 11/1993 | Brass et al. | |
| 5,279,150 A * | 1/1994 | Katzer et al. | 494/10 |
| 5,316,667 A | 5/1994 | Brown et al. | |
| 5,322,620 A | 6/1994 | Brown et al. | |
| 5,653,887 A | 8/1997 | Wahl et al. | |
| 5,741,213 A | 4/1998 | Kouchi et al. | |

(Continued)

FOREIGN PATENT DOCUMENTS

EP    0 392 475    10/1990

(Continued)

OTHER PUBLICATIONS

International Search Report for PCT/US2008/078274, mailed Dec. 29, 2008.

(Continued)

*Primary Examiner* — Walter Griffin
*Assistant Examiner* — Timothy Cleveland
(74) *Attorney, Agent, or Firm* — John R. Merkling; Edna M. O'Connor; Laura B. Arciniegas (57) ABSTRACT

A centrifugal blood separation apparatus having an optical camera control system with a focused, stationary light source. A diffusion plate mounted on a rotor, rather than on or near the light source, allows an intense light beam to be transmitted from the light source to the rotor and then diffused at the rotor across an observation region. Different characteristics of a diffusion surface allow different lighting regions within the observation region. The diffusion plate has upper and lower plates with a diffusion surface sealed between the plates. This prevents degradation or contamination of the diffusion surface by abrasion, dirt, blood components or other materials that might incidentally contact the diffusion surface.

25 Claims, 6 Drawing Sheets

U.S. PATENT DOCUMENTS

| | | | |
|---|---|---|---|
| 5,814,279 | A | 9/1998 | Biesel et al. |
| 5,930,033 | A | 7/1999 | Inoue et al. |
| 6,002,474 | A | 12/1999 | Thomas et al. |
| 6,053,856 | A | 4/2000 | Hlavinka |
| 6,334,842 | B1 | 1/2002 | Hlavinka et al. |
| 6,506,606 | B1 | 1/2003 | Winkelman et al. |
| 6,514,189 | B1 | 2/2003 | Hlavinka et al. |
| 6,790,371 | B2 | 9/2004 | Dolecek |
| 6,862,141 | B2 | 3/2005 | Olczak |
| 7,355,685 | B2 | 4/2008 | Scibona et al. |
| 7,422,693 | B2 | 9/2008 | Carter et al. |
| 2002/0147094 | A1 | 10/2002 | Dolecek |
| 2002/0196435 | A1 | 12/2002 | Cohen et al. |
| 2003/0113930 | A1 | 6/2003 | Winkelman et al. |
| 2005/0051466 | A1 | 3/2005 | Carter et al. |
| 2006/0072111 | A1 | 4/2006 | Budd et al. |
| 2006/0082700 | A1 | 4/2006 | Gehlson et al. |
| 2006/0087649 | A1 | 4/2006 | Ogawa et al. |
| 2007/0102374 | A1 | 5/2007 | Kolenbrander et al. |

FOREIGN PATENT DOCUMENTS

| | | |
|---|---|---|
| EP | 04371245 | 12/1992 |
| EP | 0637744 | 2/1995 |

OTHER PUBLICATIONS

Salgaller, Michael, "A Manifesto on the Current State of Dendritic in Adoptive Immunotherapy", *Transfusion* 43(4):422-424, 2003.

* cited by examiner

BLOOD PROCESSING APPARATUS WITH SEALED DIFFUSER IN OPTICAL CONTROL APPARATUS

This application claims priority of U.S. Provisional application 61/014,554 filed Dec. 18, 2007. The technology of this application is related to U.S. application Ser. No. 11/867,816 "Stroboscopic LED Light Source for Blood Processing Apparatus", filed Oct. 5, 2007 and its parent case U.S. Pat. No. 7,422,693, issued Sep. 9, 2008. Further related technology is found in U.S. application Ser. No. 10/884,877, "Monitoring and Control System for Blood Processing", filed Jul. 1, 2004. The disclosures of these applications are incorporated herein by reference.

BACKGROUND OF INVENTION

Blood collection and processing play important roles in the worldwide health care system. In conventional blood collection, blood is removed from a donor or patient, separated into its various blood components via centrifugation, filtration and/or elutriation and stored in sterile containers for future infusion into a patient for therapeutic use. The separated blood components typically include fractions corresponding to red blood cells, white blood cells, platelets and plasma. Separation of blood into its components can be performed continuously during collection or can be performed subsequent to collection in batches, particularly with respect to the processing of whole blood samples. Separation of blood into its various components under highly sterile conditions is critical to most therapeutic applications.

Recently, apheresis blood collection techniques have been adopted in many blood collection centers wherein a selected component of blood is collected and the balance of the blood is returned to the donor during collection. In apheresis, blood is removed from a donor and immediately separated into its components by on-line blood processing methods. Typically, on-line blood processing is provided by density centrifugation, filtration and/or diffusion-based separation techniques. One or more of the separated blood components are collected and stored in sterile containers, while the remaining blood components are directly re-circulated to the donor. An advantage of this method is that it allows more frequent donation from an individual donor because only a selected blood component is collected and purified. For example, a donor undergoing plateletpheresis, whereby platelets are collected and the non-platelet blood components are returned to the donor, may donate blood as often as once every fourteen days.

Apheresis blood processing also plays an important role in a large number of therapeutic procedures. In these methods, blood is withdrawn from a patient undergoing therapy, separated, and a selected fraction is collected while the remainder is returned to the patient. For example, a patient may undergo leukapheresis prior to radiation therapy, whereby the white blood cell component of his blood is separated, collected and stored to avoid exposure to radiation. Alternatively, apheresis techniques may be used to perform red blood cell exchange for patients with hematological disorders such as sickle cell anemia and thalassemia, whereby a patient's red blood cell component is removed and donated packed red blood cells are provided to the patient along with his remaining blood components. Further, apheresis may be used to perform therapeutic platelet depletion for patients having thrombocytosis and therapeutic plasma exchange for patients with autoimmune diseases.

Both conventional blood collection and apheresis systems typically employ differential centrifugation methods for separating blood into its various blood components. In differential centrifugation, blood is circulated through a sterile separation chamber, which is rotated at high rotational speeds about a central rotation axis. Rotation of the separation chamber creates a centrifugal force directed along rotating axes of separation oriented perpendicular to the central rotation axis of the centrifuge. The centrifugal force generated upon rotation separates particles suspended in the blood sample into discrete fractions having different densities. Specifically, a blood sample separates into discrete phases corresponding to a higher density fraction comprising red blood cells and a lower density fraction comprising plasma. In addition, an intermediate density fraction comprising platelets and leukocytes forms an interface layer between the red blood cells and the plasma. Descriptions of blood centrifugation devices are provided in U.S. Pat. No. 5,653,887 and U.S. patent application Ser. No. 10/413,890.

To achieve continuous, high throughput blood separation, extraction or collection ports are provided in most separation chambers. Extraction ports are capable of withdrawing material from the separation chamber at adjustable flow rates and, typically, are disposed at selected positions along the separation axis corresponding to discrete blood components. To ensure the extracted fluid exiting a selected extraction port is substantially limited to a single phase, however, the phase boundaries between the separated blood components must be positioned along the separation axis such that an extraction port contacts a single phase. For example, if the fraction containing white blood cells resides too close to the extraction port corresponding to platelet enriched plasma, white blood cells may enter the platelet enriched plasma stream exiting the separation chamber, thereby degrading the extent of separation achieved during blood processing. Although conventional blood processing via density centrifugation is capable of efficient separation of individual blood components, the purities of individual components obtained using this method is often not optimal for use in many therapeutic applications. For example, centrifugation separation of blood samples is unable to consistently (99% of the time) produce separated platelet components which have less than $1 \times 10^6$ white blood cells per every $3 \times 10^{11}$ platelets collected. The presence of white blood cells in platelet products increases the risks of viral exposure and immunological complications upon infusion into a patient.

The purity of extracted blood components using density centrifugation is currently limited by the control of the position of phase boundary layers between separated components provided by conventional centrifugation devices and methods. The position of phase boundaries along the separation axis depends on a number of variables. First, phase boundary positions depend on the relative flow rates of individual blood components out of the separation chamber. Second, phase boundary positions depend on the rotational velocity of the separation chamber about the central rotation axis and the temperature of the blood undergoing separation. Third, phase boundary positions vary with the composition of the blood undergoing processing. Blood sample composition may vary considerably from donor to donor and/or from patient to patient. In addition, blood composition may vary significantly as function of time for a given donor or patient, especially as blood is recycled through the separation chamber multiple times. Given the sensitivity of the phase boundary position to many variables, which change from person to person and during processing, it is important to monitor the position of the phase boundaries during blood processing to ensure optimal separation conditions are maintained and the desired purity of selected blood components is achieved. In addition, accurate characterization of the positions of phase boundaries allows for separation conditions to be adjusted and optimized for changes in blood composition during processing.

It will be appreciated from the foregoing that a need exists for methods and devices for monitoring and controlling the processing of whole blood samples and blood component samples. Particularly, optical monitoring methods and devices are needed which are capable of accurately characterizing the separation, extraction and collection of blood components processed by density centrifugation, including providing controlled stroboscopic light sources with consistent duration and intensity of illumination. An effective light source and a control mechanism are disclosed in U.S. application Ser. No. 10/905,353 and its divisional application Ser. No. 11/867,816. These applications provide stroboscopic LED light sources for use with devices for improving the processing of fluids, such as blood, components of blood and fluids derived from blood. The application relates to apparatus for controlling the processing of blood into blood components, particularly components for stroboscopic LED light sources for centrifuges. The stroboscopic apparatus comprises a first light source with reflective surfaces spaced around a central illumination axis, and light-emitting diodes spaced away from the axis radially outward from the reflective surfaces. An additional light source comprises a modified parabolic reflector surrounding a light emitting diode, the parabolic reflector having walls spaced outwardly from an axis of symmetry such that focal points fall radially outwardly from a center of the LED, forming a circular focal area. A controller that energizes the diodes for selected periods of time comprises a pair of switches connected in series, with an LED connected between the switches. One of the switches is connected to ground and is closed at the end of a period of illumination.

An exemplary optical monitoring system for a density centrifuge having a separation chamber rotating about a central rotation axis comprises at least one light source, a light collection element and a detector. Rotation of the separation chamber about a central rotation axis results in separation of the blood components in the separation chamber according to density along rotating separation axes oriented perpendicular to the central rotation axis of the centrifuge. Both the light source and light collection element are arranged such that they are periodically in optical communication with an observation region positioned on the density centrifuge. In one embodiment, the light source and detector are arranged such that an optical cell of the separation chamber is periodically rotated into and out of the observation region. The light sources are capable of generating an incident light beam having a selected wavelength range including, but not limited to, visible light, infrared light and/or ultraviolet light. It has been found, however, that diffusing a focused, columnar light beam near the observation region can improve performance.

SUMMARY OF THE INVENTION

The present invention provides a centrifugal blood processing system with an optical control system. The control system includes at least one stationary light source mounted on a stationary portion of the centrifugal blood processing system for illuminating an observation region and a diffusion element mounted on a centrifuge rotor. The diffusion element translates focused, columnar light from the stationary light source into diffuse light for illuminating at least a portion of the observation region. The diffusion element may provide discrete regions that transmit diffuse light or columnar light.

A diffusion region in the diffusion element is sealed between plates, whereby the optical characteristics of the diffusion region are protected from contamination, abrasion, or other damage.

The invention is further illustrated by the following description, examples, drawings and claims.

DETAILED DESCRIPTION OF THE INVENTION

Referring to the drawings, like numerals indicate like elements and the same number appearing in more than one drawing refers to the same element. In addition, hereinafter, the following definitions apply:

"Light" refers to waves of electric and magnetic fields that also exhibit particle-like behavior. Light useful for the methods of the present invention includes gamma rays, X-rays, ultraviolet light, visible light, infrared light, microwaves, radio waves or any combination of these.

"Light collection element" refers to a device or device component that collects light and distributes the collected light in a desired way. Light collection elements useable in the present invention are capable of collecting at least a portion of transmitted light, scattered light or both generated upon illumination of an observation region on a blood-processing device. Exemplary light collection elements of the present invention are capable of collecting light in a manner generating an image of an observation region on a detector. Light collection elements of the present invention include, but are not limited to, fixed focus lenses, spherical lenses, cylindrical lenses, aspheric lenses, wide angle lenses, zoom lenses, concave lenses, convex lenses, biconcave lenses, biconvex lenses, lens systems comprising a plurality of lenses, wave guides, fiber optic couplers, reflectors, spherical mirrors, aspherical mirrors, prisms, apertures, lenses, or any combination or equivalents of these. Light collection elements of the present invention are capable of directing collected light onto another optical device or device component, such as a detector. Light collection elements include at least one lens system having a selectively adjustable field of view and/or focal length. Light collection elements can be translatable along a detection axis, which is perpendicular to a central rotation axis.

"Field of view" refers to the angular distribution of light rays, which are collected and detected by an optical detection system, such as a light collection element in optical communication with a detector. Optical detection systems of the present invention can have a fixed field of view or a field of view, which is selectively adjustable.

"Blood processing" refers to the manipulation of a blood sample or component thereof, to realize a change in composition. Blood processing includes methods of separating blood or a component thereof into components or subcomponents, leukoreduction, pathogen inactivation, blood filtering, oxygenating blood and blood components, dialysis, blood purification or clearing, pathogen removal, blood and blood component warming, blood component washing, and red blood cell deglycerolization. The present invention provides improved methods of blood processing wherein a blood sample or component thereof is separated into components or subcomponents on the basis of density, size, diffusion rate, sedimentation velocity, surface chemistry properties or combinations of these characteristics.

"Observation region" refers to an illuminated portion of an object or plurality of objects. At least a portion of transmitted light, scattered light or both from the observation region is collected by a light collection element and detected by a detector. In preferred embodiments of the present invention, the observation region is positioned on a blood-processing device, component of a blood-processing device, such as an optical cell, or a blood sample container. The size and position of the observation region is determined by the field of view of the light collection element, the position of the light collection element from the blood processing device, the area of the detector and the position of the detector with respect to the light collection element. In an embodiment, the size, shape and position of the observation region is selectively adjustable by controlling the position of the light collection element with respect to the blood processing device and the field of view of the light collection element. In an embodiment of the present invention, one or more phase boundaries between optically differentiable components are viewable in the observation region. In another preferred embodiment, at least one separated component is viewable in the observation region. In another preferred embodiment, at least one extraction port is viewable in the observation region.

"Blood sample" and "blood" are used synonymously to refer to whole blood, one or more blood component, one or more blood products, or any combination of these. "Blood component" and "blood product" as used herein include cellular components, non-cellular components of blood and combinations of cellular and non-cellular components of blood. Exemplary cellular components include but are not limited to erythrocytes (red blood cells), leukocytes (white blood cells), and thrombocytes (platelets) and combinations of these materials. Leukocytes comprise monocytes, granulocytes, agranulocytes, and lymphocytes. Exemplary noncellular components include but are not limited to plasma, dissolved salts and minerals and plasma proteins. A blood component can be further fractionated into blood sub-components.

"Epi-illumination" refers to the illumination of an object and generation of scattered light. In epi-illumination, light is directed to the object along an axis of illumination that is different than the optical axis whereby scattered light is collected and detected.

"Parallel", in a physical, non-electrical sense, refers to a geometry in which two surfaces are equidistant from each other at all points and have the same direction or curvature. Substantially parallel refers to a geometry in which angular deviations from absolute parallelism are less than 10 degrees, and preferably less than 0.5 degrees for some applications.

In the following description, numerous specific details of the devices, device components and methods of the present invention are set forth in order to provide a thorough explanation of the precise nature of the invention. It will be apparent, however, to those of skill in the art that the invention can be practiced without these specific details.

Figure 1:
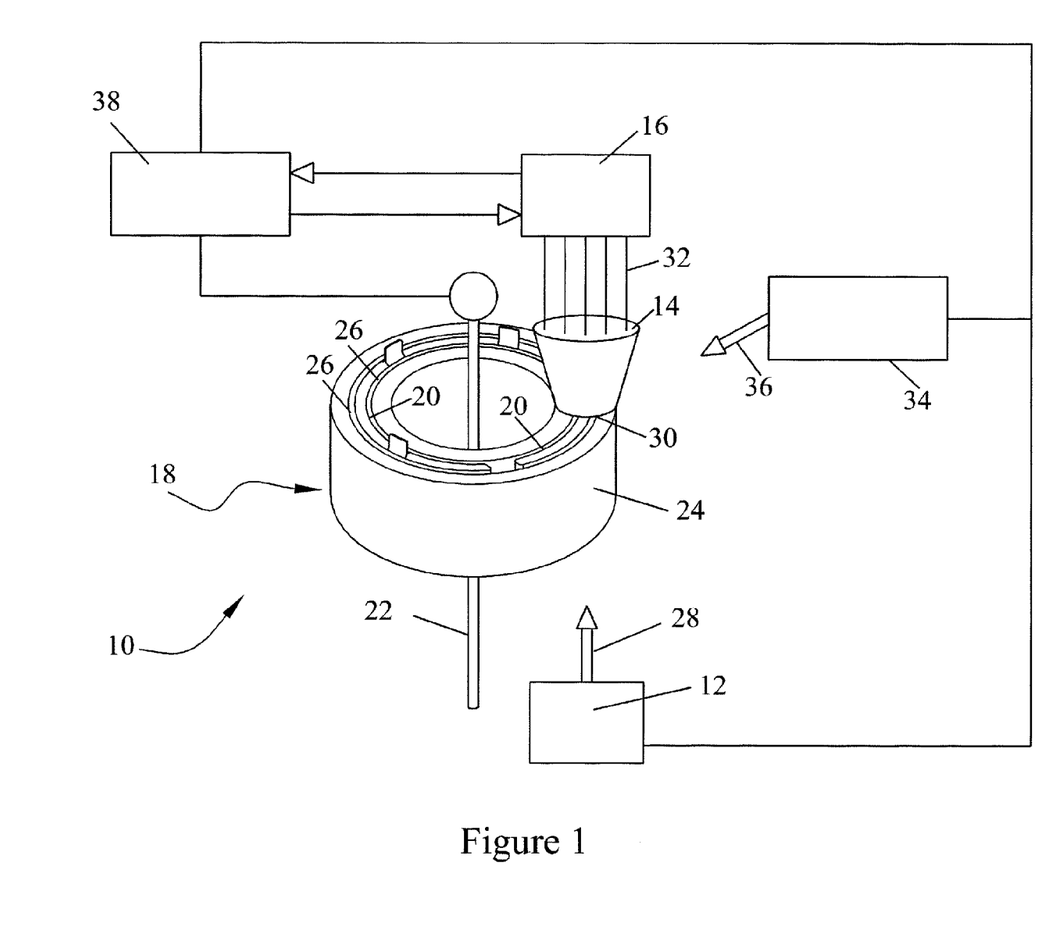
FIG. 1 is a schematic drawing showing an optical monitoring and control system.

FIG. 1 schematically illustrates an exemplary embodiment of the optical monitoring system of the present invention capable of measuring a distribution of scattered and/or transmitted light intensities corresponding to patterns of light originating from an observation region on a separation chamber. The illustrated monitoring system 10 comprises light source 12, light collection element 14, and detector or CCD camera 16. Light source 12 is in optical communication with a density centrifuge 18, which rotates about central rotation axis 22. Rotation about central rotation axis 22 results in separation of a blood sample in a separation chamber 20 into discrete blood components. The centrifuge 18 may comprise a rotor 24 having an internal, circular groove 26 wherein the separation chamber 20 is positioned and fastened. During operation of the density centrifuge, a rotating means or motor rotates both rotor and separation chamber about the central rotation axis 22. The blood sample is separated into an outer higher density phase corresponding to a red blood cell component, an intermediate density phase corresponding to a white blood cell and platelet-containing component (e.g. buffy coat), and a lower density inner phase corresponding to a platelet enriched plasma component.

Light source 12 provides incident light beam 28, which illuminates an observation region 30 on separation chamber 20, preferably in a manner generating scattered and/or transmitted light from the blood sample undergoing separation. Light source 12 is capable of generating an incident light beam, a portion of which is transmitted through at least one blood component undergoing separation in separation chamber 20. At least a portion of scattered and/or transmitted light from the observation region 30 is collected by light collection element 14. Light collection element 14 is capable of directing at least a portion of the collected light 32 onto detector 16. The detector 16 detects patterns of collected light 32 from the observation region, thereby measuring distributions of scattered and/or transmitted light intensities. Distributions of scattered and/or transmitted light intensities comprise images corresponding to patterns of light originating from the observation region 30. Images may be monochrome images, which provide a measurement of the brightness of separated blood components. Alternatively, images may be color images, which provide a measurement of the colors of separated blood components.

Observation region 30 is positioned on a portion of the density centrifuge 18, preferably on the separation chamber 20. Separated blood components and phase boundaries between optically differentiable blood components are viewable in observation region 30. The observation region is positioned on an optical cell of the separation chamber having windows for transmitting the incident beam through the blood sample undergoing processing. One or more extraction ports (not shown) are viewable in observation region 30. The observation region 30 may be positioned on a portion of the separation chamber such that the composition of a separated blood component can be directly monitored. The monitoring system provides a method of characterizing the type of cellular component collected and counting the amount of cells extracted from the separation chamber as a function of time. The monitoring system may also directly measure the concentration of non-cellular blood components, such as blood plasma proteins.

Optionally, the observation region 30 can also be illuminated by epi-illumination light source 34, which is positioned on the same side of the separation chamber as the light collection element and detector. Epi-illumination light source 34 generates an incident beam 36, which is scattered by the blood sample and/or centrifuge. A portion of the light from epi-illumination light source 34 scattered by the separation chamber and is collected by light collection element 14 and detected by detector 16.

Detector 16 generates output signals corresponding to the measured distributions of scattered or transmitted light intensities or images. Detector 16 is operationally connected to a centrifugation device controller 38 capable of receiving the output signals. Centrifugation device controller 38 displays the measured intensity distributions, stores the measured intensity distributions, processes measured intensity distributions in real time, transmits control signals to various optical and mechanical components of the monitoring system and centrifuge or any combination of these. Centrifugation device controller 38 is operationally connected to centrifuge 18 and is capable of adjusting selected operating conditions of the density centrifuge, such as the flow rates of cellular and non-cellular components out of the separation chamber, the position of one or more phase boundaries along the separation axes, rotational velocity of the separation chamber about central rotation axis 22, the infusion of anticoagulation agents or other blood processing agents to the blood sample, or any combination of these.

As shown in FIG. 1, centrifugation device controller 38 can also be operationally connected to light source 12 and/or epi-illumination light source 34. In this embodiment, centrifugation device controller 38 and detector 16 are capable of generating output signals for controlling illumination conditions. For example, output signals from detector can be used to control the timing of illumination pulses, illumination intensities, the distribution of illumination wavelengths or position of light source 12 or epi-illumination light source 34.

Light sources comprise light emitting diodes (LEDs) capable of generating one or more incident beams for illuminating an observation region on the density centrifuge. A plurality of LEDs may be positioned to illuminate a single side or multiple sides of a density centrifuge. Light sources useable in the present invention include light emitting diodes and arrays of light emitting diode light sources. Use of light emitting diode light sources is preferred for some applications because they are capable of generating precisely timed illumination pulses. Preferred light sources generate an incident light beam having a substantially uniform intensity. Light sources of the present invention generate an incident beam having a selected wavelength range and selected intensity.

The optical monitoring system comprises a plurality of light sources, each capable of generating an incident light beam having a different wavelength range. For example, the optical monitoring system comprises a combination of any of the following: white light source, red light source, green light source, blue light source and infra red light source. Use of a combination of light sources having different wavelength ranges is beneficial for discriminating and characterizing separated blood fractions because absorption constants and scattering coefficients of cellular and non-cellular components of blood vary with wavelength. For example, a red blood cell component is easily distinguished from platelet-enriched plasma component by illumination with light having wavelengths selected over the range of about 500 nm to about 600 nm because the red blood cell component absorbs light over this wavelength significantly more strongly that the platelet-enriched plasma component. In addition, use of multiple colored light sources for illumination provides a means of characterizing the white blood cell type in an extracted blood component. As different white blood cell types have different absorption and scattering cross sections at different wavelengths, monitoring transmitted and/or scattered light from a white cell-containing blood component provides a means of distinguishing the various white blood cell types in a blood component and quantifying the abundance of each cell-type.

The light sources provide a continuous incident light beam or a pulsed incident light beam. Pulsed light sources are capable of being switched on and off synchronous with the rotation of the separation chamber. The illumination system also includes one or more aperture plates capable of providing a selected illumination area on a blood processing device. An aperture plate is positioned between the light source and the blood sample undergoing separation. The aperture plate masks areas of the separation chamber where exposure to light causes unwanted scattered light. In some instances, the reduction of unwanted scattered light detected by the detector reduces noise and, therefore, improves signal-to-noise ratio and image quality. Aperture plates are typically integrated into a rotor that holds the separation chamber during rotation. The aperture plate rotates with the separation chamber. Optical filters and polarizers can also be incorporated into the illumination system of the present invention to provide illumination beams having selected optical properties, such as intensity, power, wavelength range and polarization state. Diffusers can also be incorporated into the illumination system of the present invention to provide spatially uniform illumination beams. A novel diffuser is disclosed hereafter.

Figure 2:
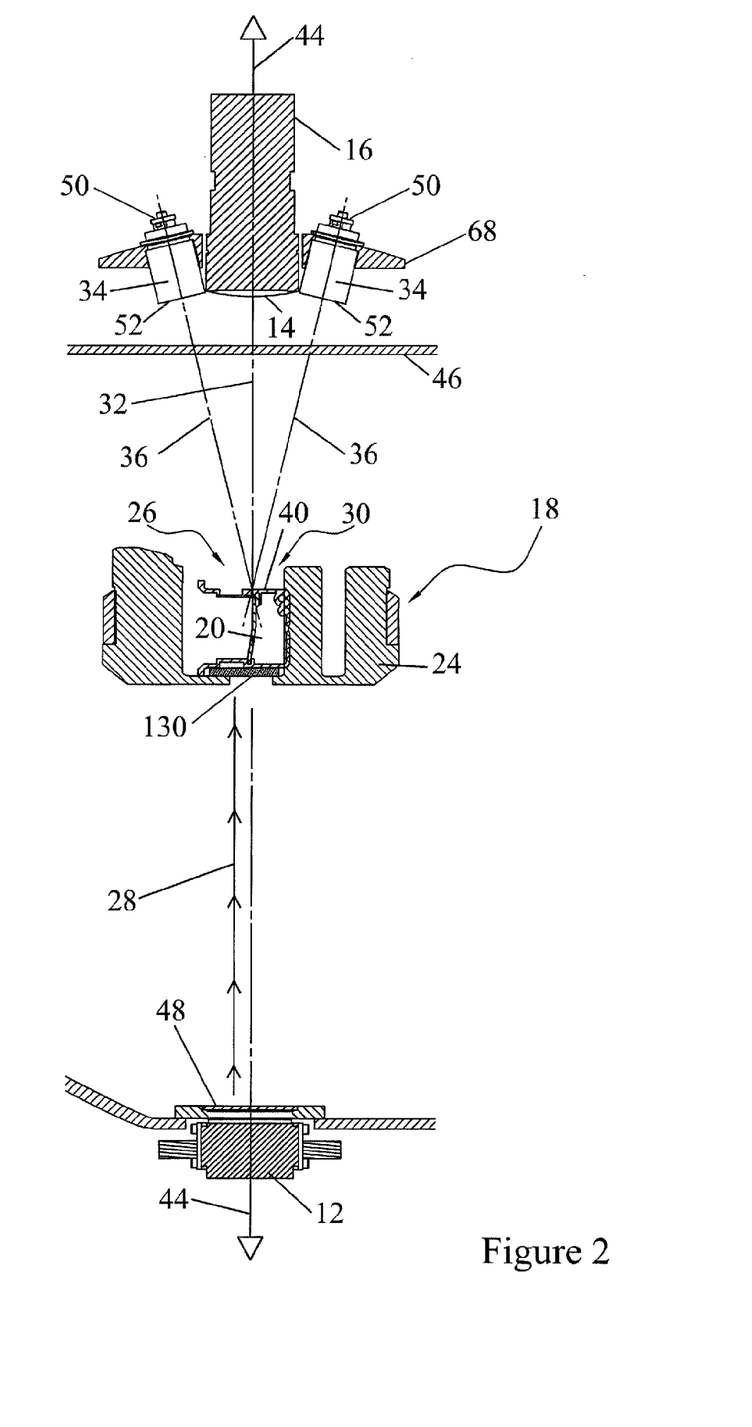
FIG. 2 is a cut away view of the optical monitoring and control system of FIG. 1.

Top pulsed LED light source 34 may be positioned about 4.26 inches from the top 40 of observation region 30, and bottom pulsed LED light source 12 is positioned about 7.47 inches from the top 40 of observation region 30. As shown in FIG. 2, CCD camera 16 is substantially co-planar with selected optical surfaces of observation region 30, such as optical surfaces corresponding to an interface monitoring region, calibration markers, one or more extraction ports and one or more inlets. The CCD camera is also separated from the center of the fixed focus lens system by a distance along optical axis 44 such that an image corresponding to selected optical surfaces of observation region 30 is provided on the sensing surface of the CCD camera. An advantage of this optical configuration is that it allows distributions of light intensities comprising images of top 40 of rotating observation region 30 to be measured and analyzed in real time.

Referring to the cross section shown in FIG. 2, first transparent plate 46 is provided between CCD camera 16 and observation region 30, and second transparent plate 48 is provided between bottom pulsed LED light source 12 and observation region 30. First and second transparent plates 46 and 48 physically isolate CCD camera 16, top pulsed LED light source 34 and bottom pulsed LED light source 12 from observation region 30 so that these components will not contact a sample undergoing processing in the event of sample leakage from the separation chamber. In addition, first and second transparent plates 46 and 48 minimize degradation of CCD camera 16, top pulsed LED light source 34 and bottom pulsed LED light source 12 due to unwanted deposition of dust and other contaminants that can be introduced to the system upon rotation of the separation chamber and rotor. Further, first and second transparent plates 46 and 48 also allow a user to optimize the alignment of the camera, top pulsed LED light source and bottom pulsed LED light source without exposure to a blood sample in the separation chamber. First and second transparent plates 46 and 48 can comprise any material capable of transmitting at least a portion of upper and bottom illumination light beams 36 and 28. Exemplary materials for first and second transparent plates 46 and 48 include, but are not limited to, glasses such as optical quality scratch resistant glass, transparent polymeric materials such as transparent plastics, quartz and inorganic salts.

Figure 3:
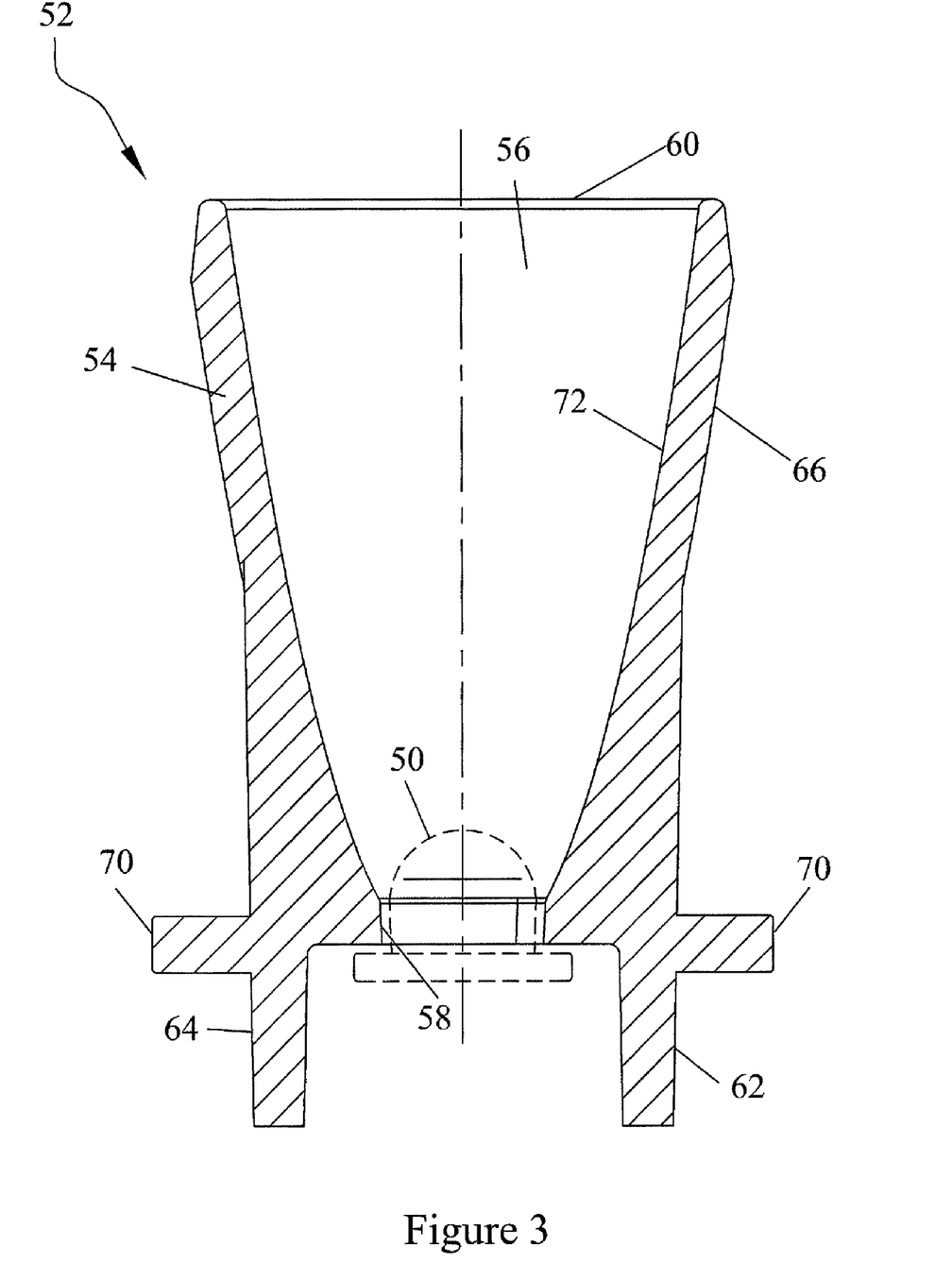
FIG. 3 is a cross sectional view of a parabolic reflector of FIG. 2.

Top pulsed LED light source 34 and bottom pulsed LED light source 12 in the optical monitoring and control system illustrated in FIG. 2 each comprise a plurality of LEDs, such as a LED array light source. Top pulsed LED light source 34 comprises LEDs 50, each equipped with a parabolic reflector 52 to provide beam collimation. An exemplary parabolic reflector 52 is shown in FIG. 3. The reflector 52 comprises a generally frustro-conical body 54 surrounding a cavity 56, the cavity having a proximal opening 58 for receiving an LED device 50 and a distal mouth 60. A pair of proximally extending fins 62, 64 on an outer surface 66 of the reflector engage the LED 50. A snap ring 70 is spaced radially symmetrically around the outer surface 66 of the reflector. The struts fit into holes (not shown) in a plate 68 (see FIG. 2) that supports the LEDs 50. Light from the LED is reflected from a parabolic mirrored surface 72 in the cavity 56.

Figure 4:
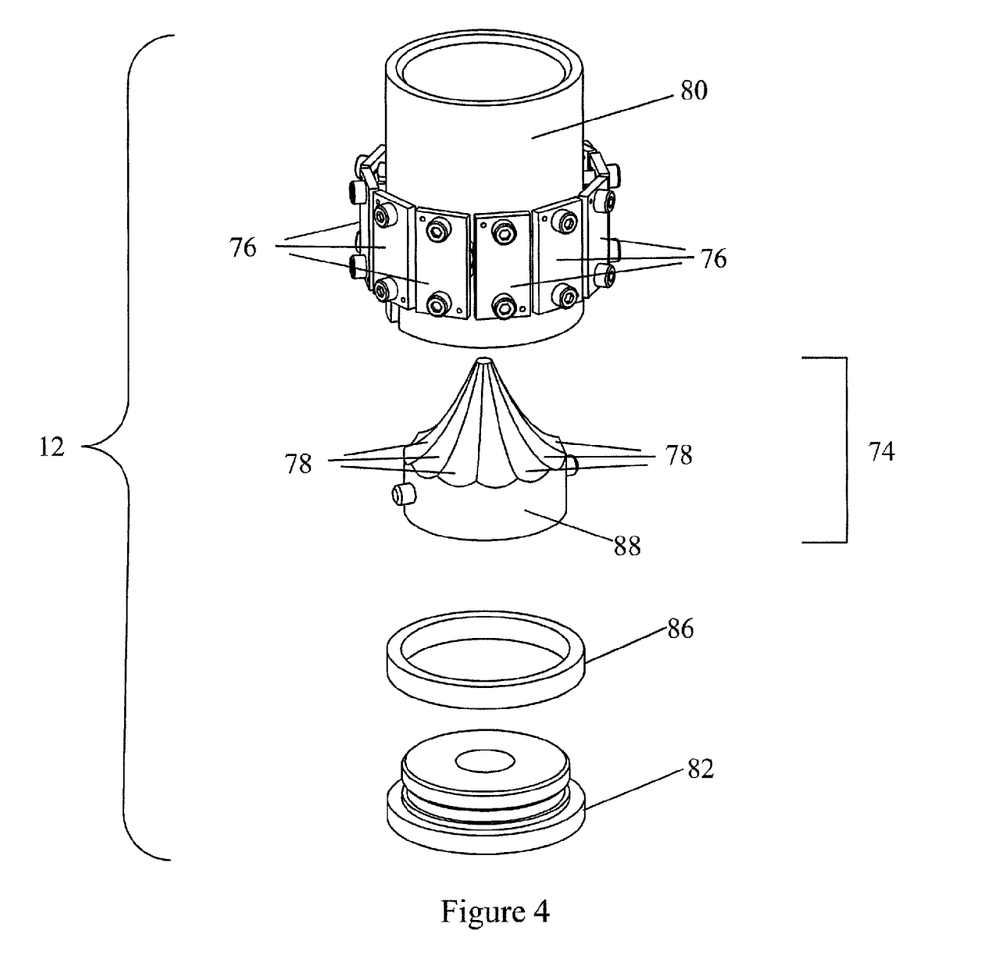
FIG. 4 provides a schematic diagram of an exploded, side view of a bottom pulsed LED light source.

Bottom pulsed LED light source 12 comprises a plurality of LEDs and a collimating optical element, such as one or more lenses, parabolic reflectors or a combination of these elements. FIG. 4 provides an exploded, side view of a bottom pulsed LED source 12. The illustrated pulsed LED light source comprises a collimating optical element 74 in optical communication with elements 76 of an LED array. As shown in FIG. 4, collimating optical element 74 is a multifaceted parabolic reflecting and collimating element comprising a plurality of contoured reflective surfaces 78, each of which is positioned in optical communication with a LED light element 76. Contoured reflective surfaces 78 have a modified parabolic contour profile in one embodiment of the present invention useful for monitoring and controlling blood processing. Depending on the contour profile selected for contoured reflective surfaces 78, collimating optical element 74 may be configured to provide a plurality of incident beam propagating along propagation axes that are approximately parallel or a plurality of incident beam propagating along propagation axes which are not parallel.

The LED light source 12 comprises a cylindrical frame 80 supporting LED light elements 76 symmetrically around the outer surface of the frame. A base 82 may be secured in a proximal end 84 of the frame 80 by any suitable means, such as threading, a pressure fit, a spacer 86 (FIG. 4), or other means. The contoured reflective surfaces 78 are formed in a mirror assembly 88. The LED light elements 76 are mounted in the frame such that light producing parts of an LED are in or near the focal region of the adjacent surface 78.

Top pulsed LED light source 34 and bottom pulsed LED light source 12 are capable of providing synchronized light pulses having accurately selectable temporal characteristics. Pulse widths of light pulses useable in the present invention depend on the rotational velocity of the density centrifuge. Typically, the smaller the pulse width of the light pulse, the less blurring of the optical image corresponding to the acquired distribution of light intensities. However, larger pulse widths allow more photons to be integrated by the CCD of the camera and, thus, provide enhanced signal-to-noise ratios. For a rotational velocity equal to about 3000 RPM, pulse widths less than about 8 microseconds are useful for minimizing blurring of the image of the optical cell generated. Exemplary light pulses useful for some applications of the present invention have pulse widths selected over the range of about 0.2 microsecond to about 50 microseconds.

CCD camera 16 comprises a monochrome or color CCD camera positioned a fixed, selected distance from a fixed focus lens system. CCD camera 16 can be contained in a housing capable of maintaining the selected separation distance between these elements and also capable of minimizing detection of unwanted scattered light. An exemplary CCD camera is the "Flea" manufactured by Point Grey Research, Inc. and has a pixel area equal to about 70 pixels by 768 pixels. An exemplary lens comprises an F 2.8 fixed focal length lens system having a focal length of 28 millimeters manufactured by Schneider Optics, Inc. This combination of optical components provides a field of view equal to about ⅜ inch by ½ inch and a depth of field selected over the range of about 1/16 inch to about ½ inch. This field of view and depth of field allows for measurement of distributions of light intensities comprising images of observation region 30 for monitoring and controlling the positions of phase boundary positions in an interface region and the compositions of cellular material exiting one or more extraction port.

Figure 5:
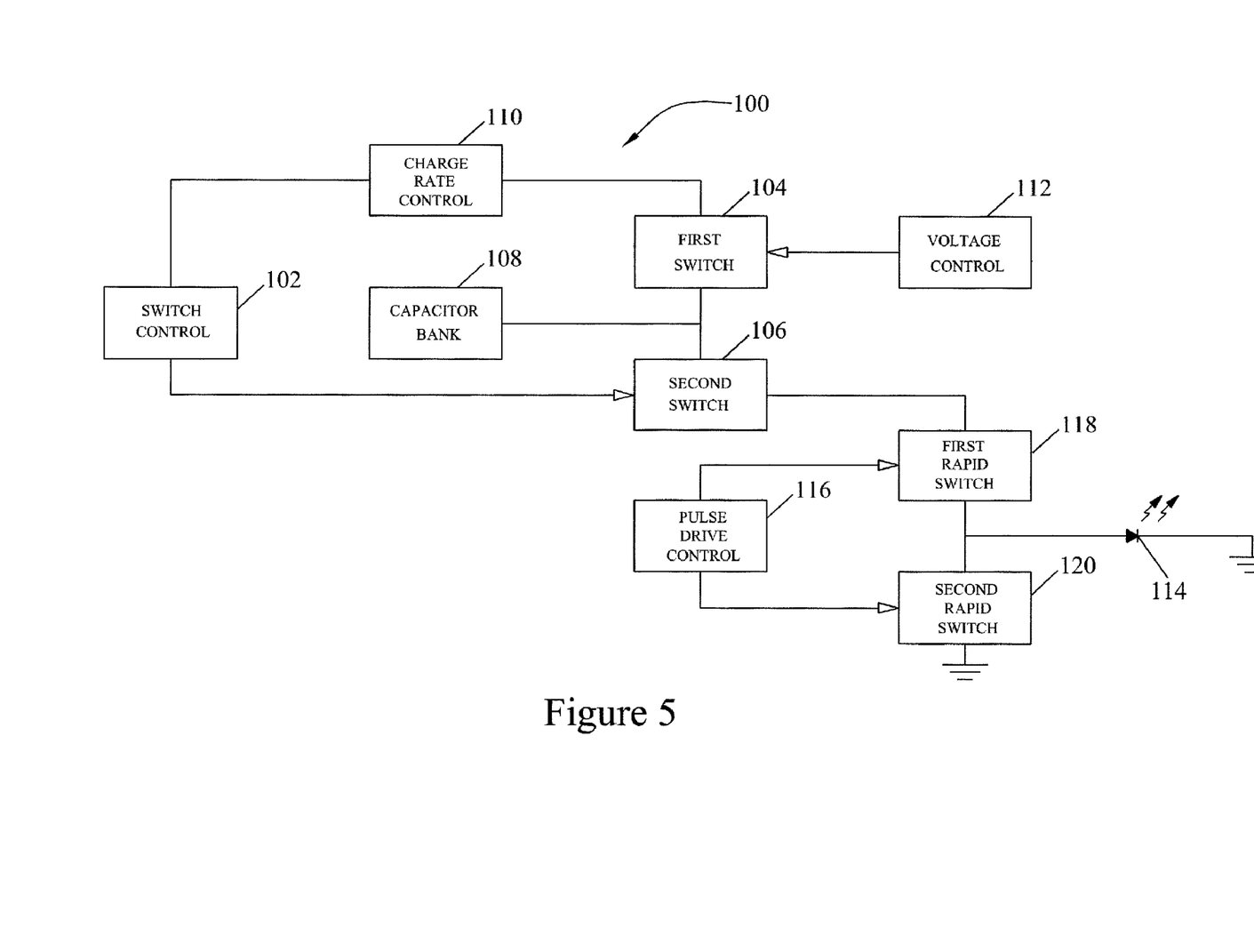
FIG. 5 is a functional block diagram of a control circuit.

The LED light sources are controlled by control circuits, such as control circuit 100, illustrated in functional block diagram in FIG. 5. A control circuit 100 may control all or any subset of the LED light sources. Preferably, however, a single control circuit controls two LED devices having the same frequency characteristics and positioned so that the failure of one LED device would not significantly affect the function of the apparatus as a whole. The control circuit 100 comprises a switch control unit 102 that selectively opens and closes a first switch circuit 104 and a second switch circuit 106 in response to signals from a microprocessor to maintain a selected charge on a bank 108 of power capacitors. The first switch circuit 104 is initially closed to charge the capacitor bank 108 while the second switch circuit 106 is open. A charging rate control circuit 110 limits the rate at which charge can be transferred to the capacitor bank 108. This prevents a sudden current demand as the system is initialized. Such a sudden demand might interfere with other power demands of the system as a whole. The charging rate may be fixed and not programmable, while other parameters of the control circuit 100 are programmable. The charging rate could be made programmable by using the digital circuit that adjusts the voltage stored on the capacitor bank 108. The microprocessor could then control charging by ramping the setting of the digital circuit at the programmed, controlled rate of change.

A voltage control circuit 112 regulates the peak voltage stored on the capacitor bank 108. The microprocessor selects the voltage stored on the capacitor bank 108 and preferably adjusts a digitally controllable device in the voltage control circuit. After the capacitor bank 108 is charged to its selected voltage, first switch circuit 104 can be left closed, allowing charging to continue during normal operation, and second switch circuit 106 can be closed, providing driving power to the LED devices through other circuit components, as explained below. The switch control unit 102 provides timing and control signals to close the first switch circuit 104 and to close the second switch circuit 106. When both switch circuits 104 and 106 are closed, power is established within the capacitor bank 108.

With second switch circuit 106 closed, power is available to the LED device or devices 114. Responsive to signals from the microprocessor, a pulse drive controller 116 controls first rapid response switch 118 and second rapid response switch 120, which bracket the LED device 114. Each of the rapid response switches 118, 120 is configured to turn on or off in such a manner to provide a well-defined square power wave to the LED device 114. With the second rapid response switch open, the first response switch can be closed to provide a path for current from the capacitor bank 108 through the LED device 114 to ground. After the selected illumination period, the pulse drive controller 116 briefly turns off both switches 118, 120, and then opens the second rapid response switch 120 to ground, draining any remaining power away from the LED device 114, and sharply and precisely turning the LED device 114 off.

The apparatus described above produces a sharply timed beam of light from the columnated bottom light source 12. It has been found that this light should be diffused in the immediate vicinity of the observation region 30. A novel diffusion plate 130 mounted on the rotor 24, rather than on or near the light source 12, allows an intense light beam 28 to be transmitted from the light source 12 to the rotor 24 and then diffused at the rotor across the observation region 30. Different characteristics of a diffusion surface allow different lighting regions within the observation region 30. The diffusion plate 130 further comprises two plates 132, 134 with a diffusion surface 136 sealed between the plates. This prevents degradation or contamination of the diffusion surface by abrasion, dirt, blood components or other materials that might incidentally contact the diffusion surface.

As shown in FIG. 2, the diffusion plate 130 is mounted on the rotor 24 below the observation region 30 and the separation chamber 20. The incident beam 28 from the lower light source 12 crosses the gap between the light source and the rotor as a focused, columnated beam with relatively low loss of intensity. At the diffusion plate, the beam 28 is spread to fill the observation region relatively uniformly (or in a controlled manner, with specific characteristics in specific regions), thus allowing the camera 16 to obtain an image of the fluid separation throughout the observation region.

Figure 6:
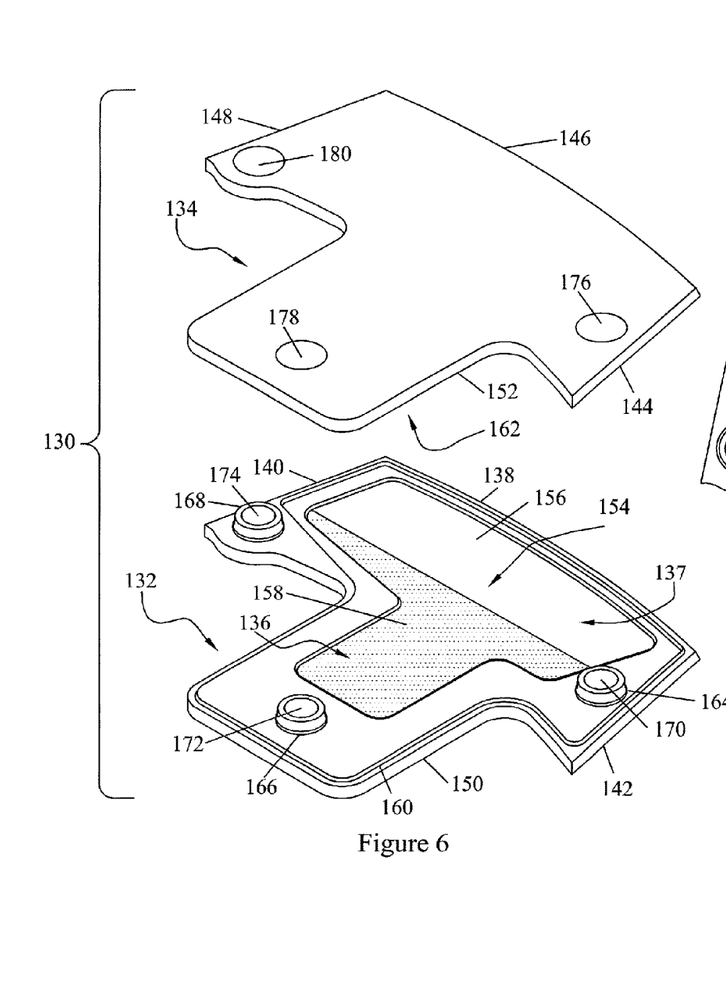
FIG. 6 is an inverted, exploded perspective view of a diffusion plate.
Figure 7:
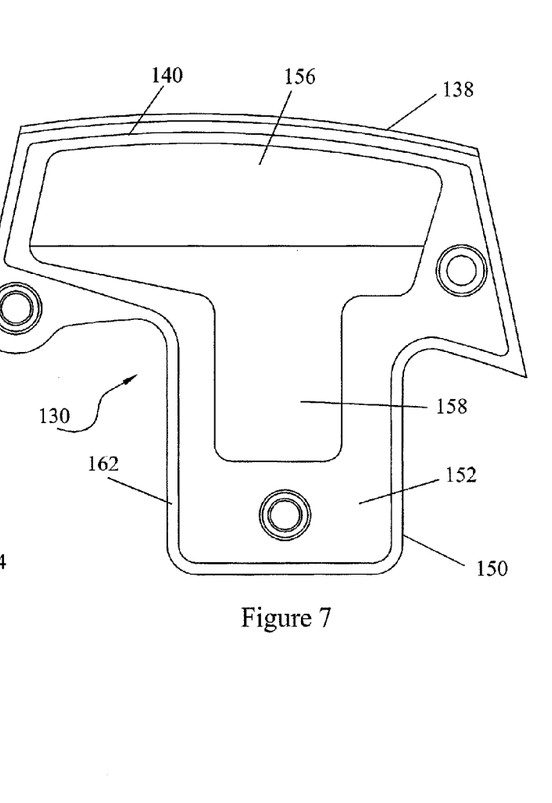
FIG. 7 is a plan view of the assembled diffusion plate of FIG. 6.

As shown in FIG. 6 and FIG. 7, the diffusion plate 130 comprises two matching plates, a plate 132 that is mounted adjacent the observation region 30 and which is called herein the "upper" plate 132, and a plate 134 that faces the lower light source 12 and which is called herein the "lower" plate 134. FIG. 6 is an inverted, exploded perspective view of the diffusion plate. "Upper" and "lower" refer to the orientation of the diffusion plate when mounted on the rotor, according to the preferred embodiment, which is reversed as to the view of FIG. 6. At least one plate, for example the upper plate 132 has an internal cavity 137. The plates have a general "T" shape, with curved edges 138, 140 that conform generally to the circumference of the rotor 24. Leading edges 142, 144 adjacent the direction of rotation of the rotor and trailing edges 146, 148 flare outward from each other radially inwardly from the curved edges 138, 140. This provides a wedge action when centrifugal force generated by the spinning rotor 24 pushes the diffusion plate 130 radially outward into a tapered cavity (not shown) in the rotor. The wedge action seats the diffusion plate more rigidly on the rotor in response to centrifugal force from the spinning rotor. Rectangular sections 150, 152 extend radially inwardly and are configured to lie under the outlet ports of the separation chamber 20. Outward sections of the diffusion plate 130 adjacent the curved edges 138, 140 are configured to lie under areas of the separation chamber where blood separates into component layers of red blood cells, buffy coat and plasma. At least one interior surface of the upper and lower plates 132, 134, for example surface 154 of internal cavity 137 in upper plate 132, has optical surface treatment. The surface 154 may have different optical properties in different regions. For example, an outward region 156 may have a polished surface, allowing intense, focused light to illuminate the relatively thick component layers. An inward region 158 under the outlet ports may have a textured surface, diffusing and reducing the intensity of the light illuminating the relatively thin and more translucent outlet ports. The different surface treatments allow the light received by the camera to be relatively uniform across the camera's field of view. This prevents high intensity light in one region from overwhelming lower intensity light in another region.

The optical characters of the outward and inward regions 156, 158 are generally determined by the molds used in forming the plate 132. Effective surface treatment may also be achieved by chemical or laser etching, machine abrasion techniques, application of laminates, or other known methods. In particular, the textured inward region 158 may have a combination texture comprised of a rough primary surface texture and a smoother secondary surface texture. Sealing the upper and lower plates together protects the optical characteristics of both the polished outward region 156 and the textured inward region 158 by enclosing these regions between the two plates. A peripheral ridge 160 on the upper plate 132 provides plastic material for ultrasonic welding joining the two plates. A peripheral groove 162 in the lower plate 134 receives any excess material from the welding process. Raised bosses 164, 166, 168 on the upper plate 132, the bosses having through bores 170, 172, 174 for receiving machine screws (not shown), fit into holes 176, 178, 180 in the lower plate 134. The bosses allow the machine screws to fasten the assembled diffusion plate 130 to the rotor without distorting the cavity formed between the upper and lower plates 132, 134.

It will be apparent that this diffusion plate 130 with an internal sealed diffusion surface protects the diffusion surface from contamination or damage by abrasion, dust, blood components or other means that might impair the diffusion surface. Multiple regions having different optical characteristics allow a single camera to record a field of view that otherwise might have too great a variation in optical intensity. Placement of the diffusion plate on the rotor, rather than adjacent a stationary light source, allows stroboscopic light to be transmitted efficiently a relatively long distance from the light source to the rotor and to be given selected characteristics, such as diffuse of focused light, in the immediate vicinity of the field of view.

It will be apparent to those skilled in the art that various modifications and variations can be made to the structure and methodology of the present invention without departing from the scope or spirit of the invention. Rather, the invention is intended to cover modifications and variations provided they come within the scope of the following claims and their equivalents.

We claim:

1. A centrifugal blood processing apparatus comprising:
 a stationary frame;
 a rotor mounted on said frame, said rotor creating a centrifugal action for separating blood into blood components,
 a light source mounted on said stationary frame of said blood processing apparatus for providing an incident light beam for illuminating an observation region on said rotor,
 a diffusion plate mounted on said rotor adjacent said observation region, said diffusion plate comprising an optical surface, said surface having at least two regions, each region having a different optical characteristic and
 a light collection element for collecting at least a portion of light transmitted from said light source, through said diffusion plate and through said observation region.

2. The apparatus of claim 1 wherein said diffusion plate comprises an upper plate and a lower plate.

3. The apparatus of claim 2 wherein said diffusion plate comprises a cavity between said upper plate and said lower plate.

4. The apparatus of claim 3 wherein said diffusion plate comprises a surface between said upper and lower plates, said surface having a selected optical characteristic.

5. The apparatus of claim 4 wherein the surface has a diffusion characteristic.

6. The apparatus of claim 4 wherein the surface has a polished characteristic.

7. The apparatus of claim 4 wherein the surface has at least two regions, each region having a different optical characteristic.

8. The apparatus of claim 7 wherein at least one region has a diffusion optical characteristic.

9. The apparatus of claim 8 wherein at least one region has a polished optical characteristic.

10. The apparatus of claim 2 wherein said diffusion plate comprises an interior surface, said surface having a selected optical characteristic.

11. The apparatus of claim 10 wherein the surface has a diffusion characteristic.

12. The apparatus of claim 10 wherein the surface has a polished characteristic.

13. The apparatus of claim 10 wherein the surface has at least two regions, each region having a different optical characteristic.

14. The apparatus of claim 13 wherein at least one region has a diffusion optical characteristic.

15. The apparatus of claim 14 wherein at least one region has a polished optical characteristic.

16. The apparatus of claim 1 wherein at least one region has a diffusion optical characteristic.

17. The apparatus of claim 1 wherein at least one region has a polished optical characteristic.

18. A centrifugal blood processing apparatus comprising:
a stationary frame;
a rotor mounted on said frame, said rotor creating a centrifugal action for separating blood into blood components, said rotor being adapted to receive a separation chamber containing a fluid, said separation chamber having an observation region,
a light source mounted on said stationary frame of said blood processing apparatus for providing an incident light beam for illuminating said observation region on said rotor,
a diffusion plate mounted on said rotor and below said observation region of said separation chamber, and
a light collection element for collecting at least a portion of light transmitted from said light source, through said diffusion plate and through said observation region.

19. The apparatus of claim 18 wherein said diffusion plate comprises an upper plate and a lower plate.

20. The apparatus of claim 19 wherein said diffusion plate comprises a cavity between said upper plate and said lower plate.

21. A centrifugal blood processing apparatus comprising:
a stationary frame;
a rotor mounted on said frame, said rotor creating a centrifugal action for separating blood into blood components, said rotor having a groove for receiving a separation chamber, said separation chamber having an observation region,
a light source mounted on said stationary frame of said blood processing apparatus for providing an incident light beam for illuminating said observation region on said separation chamber,
a planar diffusion plate mounted on said rotor adjacent said circular groove, and
a light collection element for collecting at least a portion of light transmitted from said light source, through said diffusion plate and through said observation region of said separation chamber.

22. The apparatus of claim 21 wherein said planar diffusion plate comprises a planar upper plate and a planar lower plate, said upper and lower plates forming a sealed cavity between said upper plate and said lower plate.

23. The apparatus of claim 22 wherein at least one of said upper and lower plates comprises a surface between said upper and lower plates, said surface at least two regions, at least one region being polished and at least one other region being textured.

24. A centrifugal blood processing apparatus comprising:
a stationary frame;
a rotor mounted on said frame, said rotor creating a centrifugal action for separating blood into blood components,
a light source mounted on said stationary frame of said blood processing apparatus for providing an incident light beam for illuminating an observation region on said rotor,
a diffusion plate mounted on said rotor between said observation region and said light source, said diffusion plate comprising an upper plate and a lower plate, said upper and lower plates forming a sealed cavity between said upper plate and said lower plate, and
a light collection element for collecting at least a portion of light transmitted from said light source, through said diffusion plate and through said observation region.

25. The apparatus of claim 24 wherein at least one of said upper and lower plates comprises a surface between said upper and lower plates, said surface having at least two regions, at least one region being polished and at least one other region being textured.

* * * * *